(12) United States Patent
Stoughton et al.

(10) Patent No.: US 12,286,345 B2
(45) Date of Patent: Apr. 29, 2025

(54) FILTER ASSEMBLY

(71) Applicant: 3M INNOVATIVE PROPERTIES COMPANY, St. Paul, MN (US)

(72) Inventors: Hannah L. Stoughton, Afton, MN (US); Tommie W. Kelley, Shoreview, MN (US); Windy A. Santa Cruz, Minneapolis, MN (US); Matthew W. Gorrell, South St. Paul, MN (US); John B. Stender, St. Paul, MN (US); Christine L. McCool, St. Paul, MN (US); Michael L. Elam, Woodland Hills, CA (US); Michael S. Schuffert, Chatsworth, CA (US); Jackson H. Hedden, Hoover, AL (US); Frank Tyneski, Austin, TX (US); John M. Vernon, Malibu, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 98 days.

(21) Appl. No.: 17/273,559

(22) PCT Filed: Sep. 5, 2019

(86) PCT No.: PCT/IB2019/057505
§ 371 (c)(1),
(2) Date: Mar. 4, 2021

(87) PCT Pub. No.: WO2020/049507
PCT Pub. Date: Jun. 12, 2020

(65) Prior Publication Data
US 2021/0238032 A1 Aug. 5, 2021

Related U.S. Application Data

(60) Provisional application No. 62/728,577, filed on Sep. 7, 2018.

(51) Int. Cl.
*B28B 3/00* (2006.01)
*B01J 19/00* (2006.01)
(Continued)

(52) U.S. Cl.
CPC ........... *B82B 3/0004* (2013.01); *B01J 19/004* (2013.01); *B82B 3/0076* (2013.01); *C12Q 1/6869* (2013.01)

(58) Field of Classification Search
CPC .... B82B 3/0004; B82B 3/0071; B01J 19/004; B01D 46/0002; B01D 46/10;
(Continued)

(56) References Cited

U.S. PATENT DOCUMENTS 5,782,944 A 7/1998 Justice
5,935,282 A 8/1999 Lin
(Continued)

FOREIGN PATENT DOCUMENTS

CN 2015-07975 6/2010
JP 2014-140821 8/2014
(Continued)

OTHER PUBLICATIONS

International Search report for PCT International Application No. PCT/IB2019/057505 mailed on Jan. 3, 2020, 3 pages.

*Primary Examiner* — Grant Moubry

(57) ABSTRACT

Filter assemblies are disclosed. In particular, filter assemblies including a filter media and an overlay portion covering the filter media are disclosed. Such filter assemblies may provide both acceptable filtering capacity and cleanable visible front surfaces.

14 Claims, 2 Drawing Sheets

(51) Int. Cl.
*B82B 3/00* (2006.01)
*C12Q 1/6869* (2018.01)

(58) Field of Classification Search
CPC ........ B01D 39/1623; B01D 2239/0428; B01D 2239/0457
See application file for complete search history.

(56) References Cited

U.S. PATENT DOCUMENTS

| | | | |
|---|---|---|---|
| 6,283,308 B1 * | 9/2001 | Patil | C02F 1/444 210/488 |
| 2008/0229723 A1 * | 9/2008 | Stepp | B01D 46/10 55/501 |
| 2013/0007998 A1 * | 1/2013 | Alexander | B23P 11/00 28/112 |
| 2017/0312672 A1 * | 11/2017 | Topolenski | B01D 39/163 |
| 2019/0017012 A1 * | 1/2019 | Banju | B01D 39/2027 |
| 2019/0247775 A1 * | 8/2019 | Schuld | B01D 46/0032 |
| 2019/0308124 A1 * | 10/2019 | Neef | F02M 35/02433 |

FOREIGN PATENT DOCUMENTS

| | | |
|---|---|---|
| KR | 10-2012-0114036 | 10/2012 |
| WO | WO 1998-037988 | 9/1998 |
| WO | WO 2014-147036 | 9/2014 |
| WO | WO 2020-049522 | 3/2020 |

* cited by examiner

FILTER ASSEMBLY

CROSS REFERENCE TO RELATED APPLICATIONS

This application is a national stage filing under 35 U.S.C. 371 of PCT/IB2019/057505, filed Sep. 5, 2019, which claims the benefit of U.S. Provisional Application No. 62/728,577, filed Sep. 7, 2018, the disclosure of which is incorporated by reference in its/their entirety herein.

BACKGROUND

Filters are used for many purposes; for example, removing small suspended particulates from the air. Filter assemblies may include both a rigid frame and a filter media.

SUMMARY

In one aspect, the present disclosure relates to a filter assembly. The filter assembly includes a filter media including a web having a first and second major sides and a thickness, the web including at least one of a oleophilic material or a fire retardant material. The filter assembly also includes a filter frame, where the filter frame includes an overlay portion, the overlay portion covering at least 20% but no more than 80% of the first major surface. The overlay portion is continuous and defines a plurality of open areas. The overlay portion also includes a material different from the filter media.

DETAILED DESCRIPTION

Filter assemblies can be used in a wide range of applications. Filter assemblies can be used to install or fix a filter media in a particular location. Filter assemblies that include a frame and filter media may include handles, hooks, tabs, or other mechanical or adhesive components that can attach, store, or secure the filter assembly in its intended position. In some embodiments, the filter assembly may be configured for general air filtering purposes; for example, in a room air filtering system, a furnace filtering system, or another forced air filter system. In these embodiments, the filter frame and filter media are configured such that the filter primarily filters airborne particulates. For example, the filter media may be designed to filter particles smaller than 10 micrometers in diameter, smaller than 5 micrometers in diameter, 2.5 micrometers, or 0.3 micrometers in diameter. In some embodiments, the filter assembly may be used for a specialized purpose, such as in a commercial kitchen, for grease filtering purposes.

In commercial kitchens, grease capture in exhaust hoods may be important for health, safety, and environmental reasons. Grease buildup in and around an exhaust hood or the ducting in airflow communication with the exhaust hood may pose a fire hazard, the grease deposits being highly flammable. Exacerbating the danger, commercial exhaust hoods are configured to accommodate a large volume of air traveling through them, which can magnify the hazard should a fire start.

To mitigate the hazard, commercial kitchens typically use airflow interrupters or disrupters, such as a baffle, made of a non-flammable material, such as a metal or metal alloy like stainless steel, galvanized steel, or aluminum. The baffle prevents fire from spreading between the cooking surface and the ductwork above. Additionally, aerosolized grease travels through the complicated path created by the baffle and condenses on the surfaces, preventing grease accumulating further up in the ducts. However, this grease buildup on the baffle requires regular cleaning; otherwise, the baffle's effectiveness as both a fire barrier and a grease collector is reduced. Aesthetically, visible grease on a commercial hood baffle can also be unattractive or unappetizing in a modern open kitchen. Unfortunately, baffles cannot be cleaned in place and are heavy-often weighing several kilograms. Removing, cleaning, and reinstalling the baffles can be time consuming, labor-intensive, and dangerous.

Filter assemblies are described herein may allow for effective filtration of grease droplets generated from commercial cooking processes, while providing a surface that can be wiped to maintain a clean appearance. Filter assemblies described herein may be disposable, easily removable and installable, and lightweight.

Figure 1:
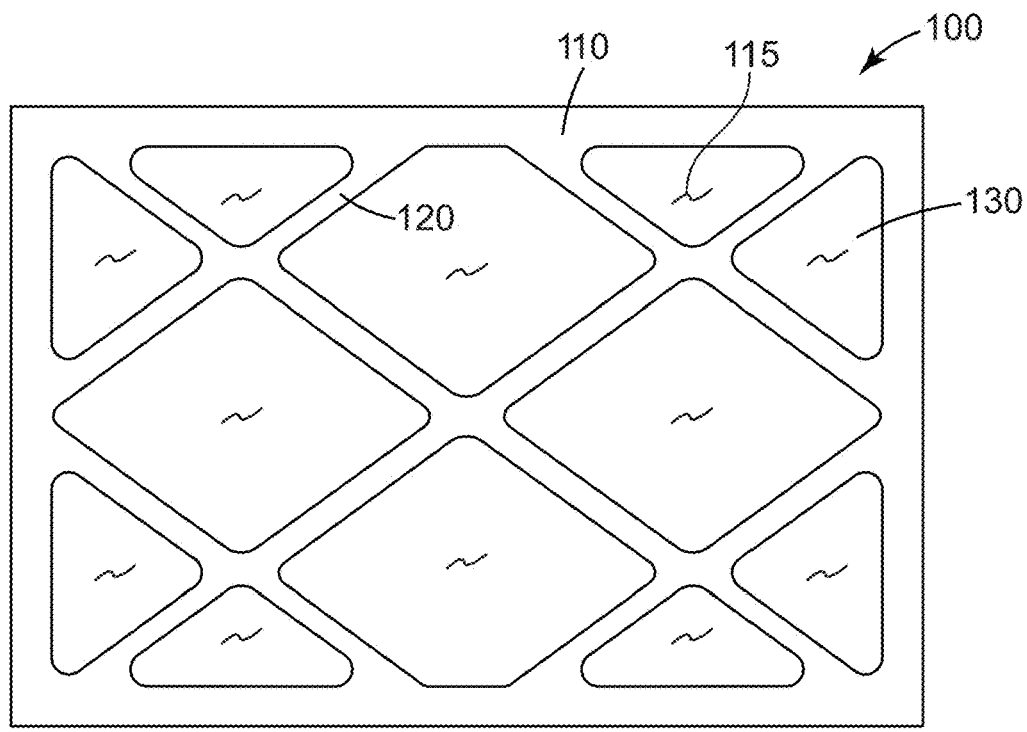
FIG. 1 is a top plan view of a filter assembly.

FIG. 1 is a top plan view of a filter assembly. Filter assembly 100 includes frame 110 including overlay portion 120, defining a plurality of open areas 130. Frame 110 (including overlay portion 120) may be any suitable material, including metal, plastic, or plastic-coated metal. In some embodiments, the material for frame 110 may be chosen for its flame resistance or high melting point. In some embodiments, the material for frame 110 may be chosen for its physical properties, such as its stiffness or rigidity. In some embodiments, frame 110 may be or include a thermoplastic. In some embodiments, frame 110 may be or include fiber reinforced plastic. In some embodiments, frame 110 may include one or more pigments or colorants. In some embodiments, frame 110 may include a coating or treatment for easy cleaning, such as a zwitterionic coating, a fluoropolymer coating, or a hydrophobic coating.

Filter assembly 100 also includes a filter made of filter media disposed adjacent or inside the frame, which is visible through the plurality of open areas (e.g., a web represented by lines 115). The filter media may be any suitable filter media, depending on desired application. In some embodiments, filter media may include a woven material or fabric. In some embodiments, filter media may include a nonwoven material. Suitable nonwoven materials may be formed through any suitable method, and with any suitable material. For example, the filter media can be non-woven (e.g., lofty, carded, air-laid, or mechanically bonded, such as spun-lace, needle-entangled, or needle-tacked), woven, knitted, mesh, or perforated film. The fibrous web or sheet can be bonded (e.g., the fibers are bonded to one another at various locations) or non-bonded. The filter media can be bonded and can include a heat-setting material or a melt material that provides some or all of the bonding in the filter, such as a flake, powder, fiber, or combination thereof, such as including any suitable thermoplastic or thermoset polymer, such as polyester, polyethylene terephthalate (PET), polypropylene (PP), or a combination thereof. After melting or heating bonding, the flake, powder, or fiber can melt and bond fibers together. The bonding of the filter media can provide increased stability and strength of the filter. The fibrous web or sheet can include any suitable material or fiber in addition to the fire-resistant fibers including oxidized polyacrylonitrile fiber (OPAN), FR rayon, or a combination thereof. For example, the filter media can include polyacrylonitrile (PAN), polyphenylene sulfide (PPS), polyethylene terephthalate (PET), polypropylene (PP), kapok fiber, poly(lactic acid) (PLA), cotton, nylon, polyester, rayon (e.g., non-flame-retardant rayon), wool, or a combination thereof. The filter media can further include a coating, a flame retardant, fibers, a heat-setting or melt material (e.g., powder, flakes, or fibers), a metal fiber, a glass fiber, a ceramic fiber, an aramid fiber, a sorbent, an intumescent material (e.g., a fiber or a particle), mica, diatomaceous earth, glass bubbles, carbon particles, or a combination thereof. Examples of fibers that can be added include larger diameter fibers that could be added to give more loft and body. Other fibers can be added to give special properties such as hollow fibers or core-sheath fibers, such as to give enhanced oleophilic or oleophobic properties to the filter. Examples of flame retardants include any polymer designated as flame-retardant or "FR", or can include (e.g., as pure materials or as compounds including the materials) aluminum, polyphosphate, phosphorus, nitrogen, sulfur, silicon, antimony, chlorine, bromine, magnesium, zinc, carbon, or a combination thereof. Flame retardants can be halogen-containing flame retardants or non-halogenated flame retardants. Examples of coatings or additives include expandable graphite, vermiculite, ammonium polyphosphate, alumina trihydrate (ATH), magnesium hydroxide (Mg(OH)2), aluminum hydroxide (Al(OH)3), molybdate compounds, chlorinated compounds, brominated compounds, antimony oxides, organophosphorus compounds, or a combination thereof. The filter media can have any suitable overall density, such as about 10 to about 400 g/m$^2$, or about 80 to about 250 g/m$^2$ or about 10 g/m$^2$ or less, or less than, equal to, or greater than about 20 g/m$^2$, 40, 60, 80, 100, 125, 150, 175, 200, 225, 250, 275, 300, 325, 350, 375, or about 400 g/m$^2$ or more.

The filter media may have any suitable thickness, from several millimeters to several centimeters, as the desired application may require. The filter includes at least one layer of the filter media including the fire-resistant fibers. The filter can include a single layer of the filter media including the fire-resistant fibers or multiple layers of the fibrous web or sheet. The multiple layers can independently be adjacent or separate within the filter. For example, the filter can include 1, 2, 3, 4, 5, 6, 7, 8, 9, or 10 or more layers of the filter media.

The filter can include other layers in addition to the one or more layers of the fibrous web or sheet including the fire-resistant fibers. The one or more additional layers can be any suitable layer, such as a fire-retardant layer (e.g., thin sheets of fire-retardant material such as Nextel™ Dot Paper, or other thin webs composed of ceramic, metal, glass or other fire-retardant/fire-resistant fibers), a non-fire-retardant layer, a woven layer, a non-woven layer, a metal layer (e.g., thin metal or foil that is perforated, or expanded metal), an adhesive layer, a coating, a powder, a sorbent layer, a gradient layer (e.g., a gradient layer that pulls grease into the interior or edges using condensation management film or thermally induced phase separation materials that have high affinity for oil/grease), a sacrificial layer (e.g., layers that could be stripped off as they become saturated with grease, with additional sacrificial layers already present or being added after stripping the disposable layer), grease-degrading layers (e.g., enzymes or microbes), a resin layer, a scrim layer, or a combination thereof. The one or more additional layers can each independently include a fire-retardant, an adhesive, a heat-setting or melt material (e.g., fiber, powder, or flake), a fire-resistant fiber, a coated fiber, powder, metal, glass, ceramic, a metal fiber, a glass fiber, an aramid fiber, a ceramic fiber, a sorbent, an intumescent material (e.g., a fiber or a particle), mica, diatomaceous earth, glass bubbles, carbon particles, or a combination thereof. The one or more additional layers can each independently be unbonded, adhesive-laminated, heat-bonded, ultrasonically bonded, needle-tacked, physically attached by fasteners, or a combination thereof.

In some instances, the filter can include materials contained between two layers of scrim. In some instances, scrim can be used to reduce shedding of fibers from the filter including the fire-resistant fibers, such as to help ensure that fibers or other loose materials from the filter do not fall into a food cooking or handling area. Examples of such materials include activated carbon, oil absorbing particles, vermiculite, or a combination thereof. Examples of scrim materials can include mesh formed from polymer or metal, nonwoven materials made from polymer, fibers (e.g., ceramic, glass, or aramid fibers), perforated film made of polymer or metal, and combinations thereof. Scrim materials can be optionally fire-resistant, such as including metals, ceramics, glass, FR rayon, OPAN, and aramid fibers (Kevlar and Nomex). Scrim materials can be coated with a fire retardant such as ammonium polyphosphate. Scrim materials that could be coated with a fire retardant can include polyethylene terephthalate (PET) or nylon.

Overlay portion 120 covers the filter media, being continuous and defining a plurality of open areas 130. In some embodiments, the overlay portion covers more than 20% but no more than 80% of the major surface of the filter media. In some embodiments, from a top plan view, the overlay portion covers more than 30%, more than 40%, more than 50%, or more than 60% of the major surface of the filter media by area. In some embodiments, the percent coverage by the overlay portion may be selected in part for a balance between maintaining a low pressure drop between the front and back sides of the filter assembly in use and also providing an aesthetically pleasing front surface appearance. Additionally, in some embodiments, sufficient surface coverage by overlay portion 120 allows the filter assembly to be wipeable. In some embodiments, overlay portion 120 has a minimum width of 2 mm. In some embodiments, overlay portion 120 has a minimum width of 10 mm. In some embodiments, overlay portion 120 has a minimum width of 5 mm. The filter media includes a material different from that over the overlay portion.

The frame, including the overlay portion, may be formed from any suitable method, including injection molding, metal injection molding, stamping, forming, punching, or any additive or subtractive process. In some embodiments, the frame is formed in separate pieces and later joined around the filter media. The frame can be removably attached through an interlocking mechanism, adhesive, or the like, or it may be permanently or semi-permanently attached through welding, rivets or other mechanical fasteners, or melting the pieces together.

Figure 2:
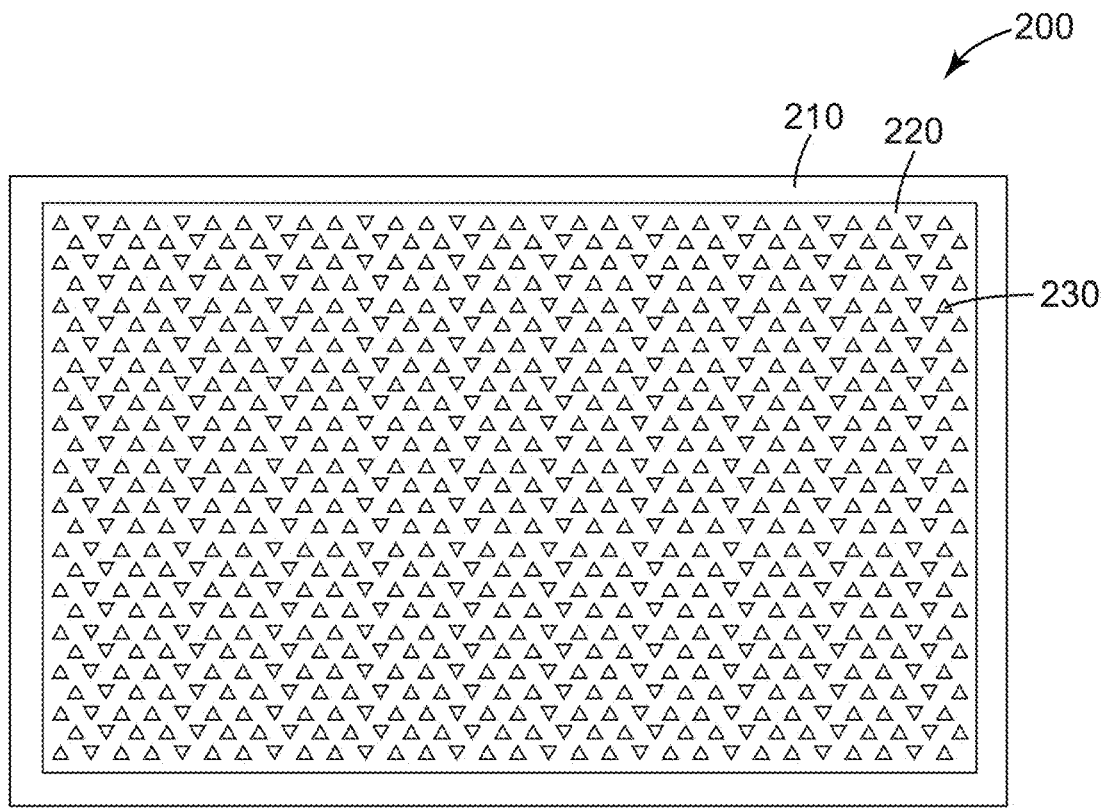
FIG. 2 is a top plan view of another filter assembly.

FIG. 2 is a top plan view of another filter assembly. Filter assembly 200 includes frame 210 including overlay portion 220, defining a plurality of open areas 230. Filter assembly 200 differs from filter assembly 100 in FIG. 1 by its different overlay portion style. In some embodiments, the plurality of open areas defined by overlay portion 220 may have a longest dimension (between points of the overlay portion) no greater than 10 mm. In some embodiments, the plurality of open areas defined by overlay portion 220 may have a longest dimension no greater than 5 mm. In some embodiments, the plurality of open areas defined by overlay portion 220 may have a longest dimension no greater than 3, 2, or even 1 mm. The open areas may have any suitable shape, including polygonal (as depicted) having any number of sides, circular, elliptical, or any other regular or irregular shape. The size, shape, and/or distribution of the open areas may vary periodically along any one of the directions of filter assembly 200, or it may vary non-periodically or appear as pseudorandom or random. Smaller apertures may hide the filter media, especially when it has absorbed grease and may not be pleasant to look at.

Figure 3:
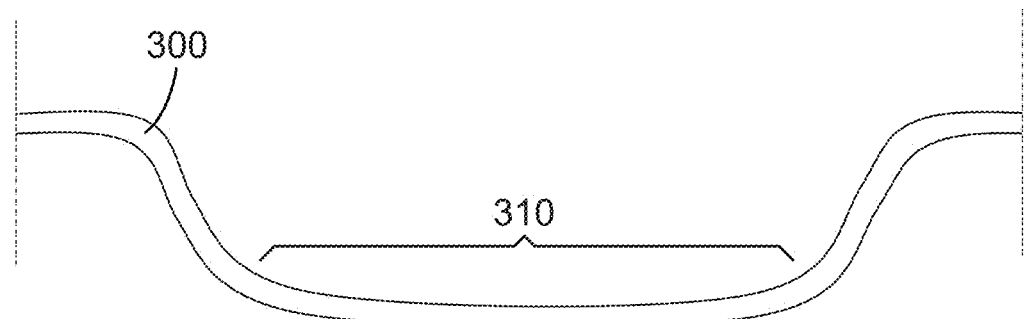
FIG. 3 is a side elevation view of a portion of an overlay portion of a filter assembly frame.

FIG. 3 is a side elevation view of a portion of a filter assembly frame. Frame portion 300 curves in the thickness direction of the filter assembly and includes flat surface portion 310. Flat surface portion 310 may be defined by portions having a radius of curvature of less than 10 cm in at least one direction. Flat surface portions may smoothly transition to non-flat portions of the overlay portion (i.e., a curve), or there may be a discontinuity between the flat surface portion and the non-flat surface portion. In some embodiments, flat surface portion 310 may, by area, make up at least 50% of the overlay portion. In some embodiments, flat surface portion 310 may, by area, make up at least 80% of the overlay portion. In some embodiments, flat surface portion 310 may, by area, make up at least 90% of the overlay portion. Flat surface portions, such as those shown in FIG. 3, may make it easier to wipe, degrease, or clean the overlay portion of the filter assembly. Small radiuses of curvature may, in some embodiments, provide crevices for grease to accumulate. Although not shown, the filter media may, in some embodiments, conform to the contours of frame portion 300, or, alternatively, may be flat or pleated below frame portion 300.

Figure 4:
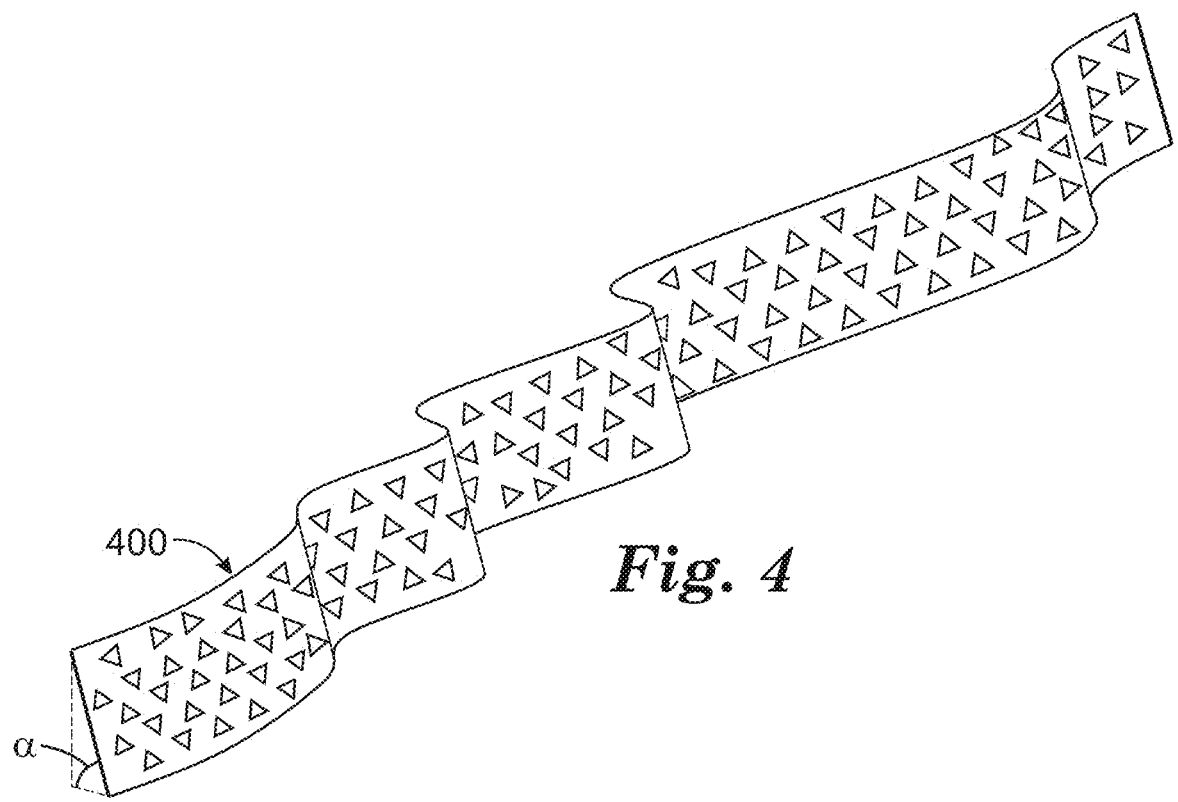
FIG. 4 is a perspective view of a portion of an overlay portion of another filter assembly frame.

FIG. 4 is a side elevation view of a portion of another filter assembly frame. Frame portion 400 exhibits angle α. Angle α is formed between the tangent plane of frame portion 400 and a reference plane normal to the thickness of the filter media. Portion 400 may be a flat surface portion. In some embodiments, a portion is a flat surface portion, as shown in FIG. 4, when the angle α varies by no more than 10 degrees from an average value of α of the flat surface portion. In some embodiments, a portion is a flat surface portion when the angle α varies by no more than 5 degrees from an average value of α of the flat surface portion. In some embodiments, a portion is a flat surface portion when the angle α varies by no more than 20 degrees from an average value of α of the flat surface portion. Such geometries may enable interesting and aesthetically pleasing filter frames while providing a flat surface for purposes of wiping or cleaning.

Descriptions for elements in figures should be understood to apply equally to corresponding elements in other figures, unless indicated otherwise. The present invention should not be considered limited to the particular examples and embodiments described above, as such embodiments are described in detail in order to facilitate explanation of various aspects of the invention. Rather, the present invention should be understood to cover all aspects of the invention, including various modifications, equivalent processes, and alternative devices falling within the scope of the invention as defined by the appended claims and their equivalents.

What is claimed is:

1. A filter assembly, comprising:
   a filter media including a web having first and second major sides, a first major surface, and a thickness, the web including at least one of an oleophilic material or a fire retardant material; and
   a filter frame, wherein the filter frame includes an overlay portion, the overlay portion covering, from a top plan view, at least 20% but no more than 80% of the first major surface by area,
   wherein the overlay portion is continuous and defines a plurality of open areas,
   wherein the overlay portion includes a material different from the filter media, and
   wherein the overlay portion curves in the thickness direction of the filter assembly and includes at least one flat surface portion, the flat surface portion defined by having a radius of curvature greater than 10 cm along at least one direction.

2. The filter assembly of claim 1, wherein the overlay portion has a minimum width of 5 mm.

3. The filter assembly of claim 1, wherein the plurality of open areas defined by the overlay portion have a longest dimension of no more than 5 mm.

4. The filter assembly of claim 1, wherein the at least one flat surface portion makes up at least 50% of the overlay portion by area.

5. The filter assembly of claim 1, wherein the at least one flat surface portion makes up at least 80% of the overlay portion by area.

6. The filter assembly of claim 1, wherein the at least one flat surface portion makes up at least 90% of the overlay portion by area.

7. The filter assembly of claim 1, wherein the overlay portion includes plastic.

8. The filter assembly of claim 1, wherein the overlay portion includes metal coated with plastic.

9. The filter assembly of claim 1, wherein the overlay portion includes metal.

10. The filter assembly of claim 1, wherein the web includes oxidized polyacrylonitrile fibers.

11. A filter assembly, comprising:
    a filter media including a web having first and second major sides, a first major surface, and a thickness, the web including at least one of an oleophilic material or a fire retardant material; and
    a filter frame, wherein the filter frame includes an overlay portion, the overlay portion covering, from a top plan view, at least 20% but no more than 80% of the first major surface by area,
    wherein the overlay portion is continuous and defines a plurality of open areas,
    wherein the overlay portion includes a material different from the filter media, and
    wherein the overlay portion includes at least one flat surface portion, wherein the at least one flat surface portion is disposed such that tangent planes forming a non-zero inclination angle with a reference plane normal to the thickness do not vary by more than 20 degrees from an average inclination angle of the at least one flat surface portion.

12. The filter assembly of claim 11, wherein the at least one flat surface portion makes up at least 50% of the overlay portion by area.

13. The filter assembly of claim 11, wherein the at least one flat surface portion makes up at least 80% of the overlay portion by area.

14. The filter assembly of claim 11, wherein the at least one flat surface portion makes up at least 90% of the overlay portion by area.

* * * * *